United States Patent
Park et al.

(10) Patent No.: US 11,098,333 B2
(45) Date of Patent: Aug. 24, 2021

(54) ATP PHOSPHORIBOSYLTRANSFERASE VARIANT AND METHOD FOR PRODUCING L-HISTIDINE USING THE SAME

(71) Applicant: CJ CheilJedang Corporation, Seoul (KR)

(72) Inventors: Myung Keun Park, Seoul (KR); Nara Kwon, Seoul (KR); Jin Nam Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/635,359

(22) PCT Filed: Aug. 2, 2018

(86) PCT No.: PCT/KR2018/008777
§ 371 (c)(1),
(2) Date: Jan. 30, 2020

(87) PCT Pub. No.: WO2019/027267
PCT Pub. Date: Feb. 7, 2019

(65) Prior Publication Data
US 2021/0010042 A1 Jan. 14, 2021

Related U.S. Application Data

(63) Continuation of application No. PCT/KR2018/008778, filed on Aug. 2, 2018.

(30) Foreign Application Priority Data

Aug. 2, 2017 (KR) .......... 10-2017-0098205

(51) Int. Cl.
C12P 13/24 (2006.01)
C12N 1/20 (2006.01)
C12N 15/77 (2006.01)

(52) U.S. Cl.
CPC ........... *C12P 13/24* (2013.01); *C12N 1/20* (2013.01); *C12N 15/77* (2013.01); *C12Y 204/02017* (2013.01)

(58) Field of Classification Search
CPC ........... C12P 13/24; C12N 1/20; C12N 15/77; C12Y 204/02017
See application file for complete search history.

(56) References Cited

U.S. PATENT DOCUMENTS

2009/0275089 A1 11/2009 Klyachko et al.

FOREIGN PATENT DOCUMENTS

| EP | 1647593 A1 | 4/2006 |
|---|---|---|
| EP | 3009505 A1 | 4/2016 |
| JP | 2005-160474 A | 6/2005 |
| KR | 10-1904666 B1 | 11/2018 |
| WO | 2014/029376 A1 | 2/2014 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Notice of Patent Grant issued in corresponding Korean Patent Application No. 10-2017-0098205 dated Sep. 12, 2018.
International Search Report issued in corresponding International Patent Application No. PCT/KR2018/008778 dated Feb. 11, 2019.
Schendzielorz et al., "Taking Control over Control: Use of Product Sensing in Single Cells to Remove Flux Control at Key Enzymes in Biosynthesis Pathways," ACS Synthetic Biology, 3: 21-29 (2014).
Kulis-Horn et al., "Corynebacterium glutamicum ATP-phosphoribosyl transferases suitable for L-histidine production—Strategies for the elimination of feedback inhibition," Journal of Biotechnology, 206: 26-37 (2015).
Mizukami et al. "Cloning of the ATP Phosphoribosyl Transferase Gene of Corynebacterium glutamicum and Application of the Gene to L-Histidine Production," Bioscience, Biotechnology, and Biochemistry, 58 (4): 635-638 (1994).
Zhang et al., "Genetic and biochemical characterization of Corynebacterium glutamicum ATP phosphoribosyltransferase and its three mutants resistant to feedback inhibition by histidine," Biochimie, 94(3): 829-838 (2012).
Kulis-Horn et al., "Histidine biosynthesis, its regulation and biotechnological application in Corynebacterium glutamicum," Microbial Biotechnology, 7: 5-25 (2013).
Extended European Search Report issued in corresponding European Patent Application No. 18841909.7 dated Mar. 15, 2021.

* cited by examiner

*Primary Examiner* — Delia M Ramirez
(74) *Attorney, Agent, or Firm* — Morgan, Lewis & Bockius LLP

(57) ABSTRACT

The present disclosure relates to an ATP phosphoribosyltransferase (HisG) protein and a method for producing histidine using the same.

15 Claims, No Drawings

Specification includes a Sequence Listing.

SEQUENCE LISTING

<160> NUMBER OF SEQ ID NOS: 13

<210> SEQ ID NO 1

<211> LENGTH: 281
<212> TYPE: PRT
<213> ORGANISM: Unknown
<220> FEATURE:
<223> OTHER INFORMATION: HisG

<400> SEQUENCE: 1

Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Asn Val Glu Phe Phe Phe Leu
        35                  40                  45

Arg Pro Lys Asp Ile Ala Ile Tyr Val Ala Gly Gly Gln Leu Asp Leu
    50                  55                  60

Gly Ile Thr Gly Arg Asp Leu Ala Arg Asp Ser Gln Ala Asp Val His
65                  70                  75                  80

Glu Val Leu Ser Leu Gly Phe Gly Ser Ser Thr Phe Arg Tyr Ala Ala
                85                  90                  95

Pro Ala Asp Glu Glu Trp Ser Ile Glu Lys Leu Asp Gly Lys Arg Ile
            100                 105                 110

Ala Thr Ser Tyr Pro Asn Leu Val Arg Asp Leu Ala Ala Arg Gly
        115                 120                 125

Leu Ser Ala Glu Val Leu Arg Leu Asp Gly Ala Val Glu Val Ser Ile
    130                 135                 140

Lys Leu Gly Val Ala Asp Ala Ile Ala Asp Val Val Ser Thr Gly Arg
145                 150                 155                 160

Thr Leu Arg Gln Gln Gly Leu Ala Pro Phe Gly Glu Val Leu Cys Thr
                165                 170                 175

Ser Glu Ala Val Ile Val Gly Arg Lys Asp Glu Lys Val Thr Pro Glu
            180                 185                 190

Gln Gln Ile Leu Leu Arg Arg Ile Gln Gly Ile Leu His Ala Gln Asn
        195                 200                 205

Phe Leu Met Leu Asp Tyr Arg Val Asp Arg Asp Asn Leu Asp Ala Ala
    210                 215                 220

Thr Ala Val Thr Pro Gly Leu Ser His Pro Gln Val Ser Pro Leu Ala
225                 230                 235                 240

Arg Asp Asn Trp Val Ala Val Arg Ala Met Val Pro Arg Arg Ser Ala
                245                 250                 255

Asn Ala Ile Met Asp Lys Leu Ala Gly Leu Gly Ala Glu Ala Ile Leu
            260                 265                 270

Ala Ser Glu Ile Arg Ile Ala Arg Ile
        275                 280

<210> SEQ ID NO 2
<211> LENGTH: 846
<212> TYPE: DNA
<213> ORGANISM: Unknown
<220> FEATURE:
<223> OTHER INFORMATION: hisG

<400> SEQUENCE: 2
atgttgaaaa tcgctgtccc aaacaaaggc tcgctgtccg agcgcgccat ggaaatcctc      60
gccgaagcag gctacgcagg ccgtggagat tccaaatccc tcaacgtttt tgatgaagca     120
aacaacgttg aatttcttct ccttcgccct aaagatatcg ccatctacgt tgctggtggc     180
cagctcgatt tgggtatcac cggccgcgac cttgctcgcg attcccaggc tgatgtccac     240

```
gaagttctttt ccctcggctt cggttcctcc actttccgtt acgcagcacc agctgatgaa      300
gagtggagca tcgaaaagct cgacggcaag cgcatcgcta cctcttaccc caaccttgtt      360
cgcgatgacc tcgcagcacg tgggctttcc gctgaggtgc tccgcctcga cggtgcagta      420
gaggtatcca tcaagcttgg tgtcgcagat gccatcgccg atgttgtatc caccggccgc      480
acgctgcgtc agcaaggtct tgcacctttc ggcgaggttc tgtgcacctc tgaggctgtc      540
attgttggcc gcaaggatga aaaggtcacc ccagagcagc agatcctgct cgccgcatc       600 cagggaattt tgcacgcgca gaacttcctc atgctggatt accgcgtcga ccgcgacaac      660
ctggacgctg ccactgcagt aaccccaggc ttatcccacc cacaggtatc cccactggca      720
cgcgacaact gggttgctgt acgcgccatg gtgccacgca ggtcagctaa cgccatcatg      780
gataagcttg ctggactcgg cgctgaagcc atcctggctt ctgaaatccg catcgcccgc      840
atctag                                                                  846
```

<210> SEQ ID NO 3
<211> LENGTH: 26
<212> TYPE: DNA
<213> ORGANISM: Artificial Sequence
<220> FEATURE:
<223> OTHER INFORMATION: Xba1-Cg1-hisG-F
<400> SEQUENCE: 3
gggtctagac ccaaacaaag gctcgc                                            26

<210> SEQ ID NO 4
<211> LENGTH: 27
<212> TYPE: DNA
<213> ORGANISM: Artificial Sequence
<220> FEATURE:
<223> OTHER INFORMATION: Xba1-Cg1-hisG-R
<400> SEQUENCE: 4
gggtctagag caaggttggc aacaacc                                           27

<210> SEQ ID NO 5
<211> LENGTH: 23
<212> TYPE: DNA
<213> ORGANISM: Artificial Sequence
<220> FEATURE:
<223> OTHER INFORMATION: Cgl13032 hisG N215R -F
<400> SEQUENCE: 5
cctcatgctg gattaccgcg tcg                                               23

<210> SEQ ID NO 6
<211> LENGTH: 23
<212> TYPE: DNA
<213> ORGANISM: Artificial Sequence
<220> FEATURE:
<223> OTHER INFORMATION: Cgl13032 hisG N215R -R
<400> SEQUENCE: 6
cgacgcggta atccagcatg agg                                               23

<210> SEQ ID NO 7
<211> LENGTH: 30
<212> TYPE: DNA
<213> ORGANISM: Artificial Sequence
<220> FEATURE:
<223> OTHER INFORMATION: Cg1-hisG-G233H/T235Q-F -continued

<400> SEQUENCE: 7
caggcttatc ccacccacag gtatccccac                                    30

<210> SEQ ID NO 8
<211> LENGTH: 30
<212> TYPE: DNA
<213> ORGANISM: Artificial Sequence
<220> FEATURE:
<223> OTHER INFORMATION: Cgl-hisG-G233H/T235Q-R

<400> SEQUENCE: 8
gtggggatac ctgtgggtgg gataagcctg                                    30

<210> SEQ ID NO 9
<211> LENGTH: 25
<212> TYPE: DNA
<213> ORGANISM: Artificial Sequence
<220> FEATURE:
<223> OTHER INFORMATION: Cgl-hisG-N215K-F

<400> SEQUENCE: 9
gctggattac aaggtcgacc gcgac                                         25

<210> SEQ ID NO 10
<211> LENGTH: 25
<212> TYPE: DNA
<213> ORGANISM: Artificial Sequence
<220> FEATURE:
<223> OTHER INFORMATION: Cgl-hisG-N215K-R

<400> SEQUENCE: 10
gtcgcggtcg accttgtaat ccagc                                         25

<210> SEQ ID NO 11
<211> LENGTH: 35
<212> TYPE: DNA
<213> ORGANISM: Artificial Sequence
<220> FEATURE:
<223> OTHER INFORMATION: Cgl-hisG-L231F/T235A-F

<400> SEQUENCE: 11
accccaggct tctccggccc agcagtatcc ccact                              35

<210> SEQ ID NO 12
<211> LENGTH: 35
<212> TYPE: DNA
<213> ORGANISM: Artificial Sequence
<220> FEATURE:
<223> OTHER INFORMATION: Cgl-hisG-L231F/T235A-R

<400> SEQUENCE: 12
agtggggata ctgctgggcc ggagaagcct ggggt                              35

<210> SEQ ID NO 13
<211> LENGTH: 281
<212> TYPE: PRT
<213> ORGANISM: Unknown
<220> FEATURE:
<223> OTHER INFORMATION: HisG

<400> SEQUENCE: 13

Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

-continued

```
Ser Leu Asn Val Phe Asp Glu Ala Asn Asn Val Glu Phe Phe Phe Leu
         35                  40                  45

Arg Pro Lys Asp Ile Ala Ile Tyr Val Ala Gly Gly Gln Leu Asp Leu
     50                  55                  60

Gly Ile Thr Gly Arg Asp Leu Ala Arg Asp Ser Gln Ala Asp Val His
 65              70                  75                      80

Glu Val Leu Ser Leu Gly Phe Gly Ser Ser Thr Phe Arg Tyr Ala Ala
             85                  90                  95

Pro Ala Asp Glu Glu Trp Ser Ile Glu Lys Leu Asp Gly Lys Arg Ile
             100             105             110

Ala Thr Ser Tyr Pro Asn Leu Val Arg Asp Asp Leu Ala Ala Arg Gly
         115                 120             125

Leu Ser Ala Glu Val Leu Arg Leu Asp Gly Ala Val Glu Val Ser Ile
     130             135             140

Lys Leu Gly Val Ala Asp Ala Ile Ala Asp Val Val Ser Thr Gly Arg
145             150             155             160

Thr Leu Arg Gln Gln Gly Leu Ala Pro Phe Gly Glu Val Leu Cys Thr
             165             170             175

Ser Glu Ala Val Ile Val Gly Arg Lys Asp Glu Lys Val Thr Pro Glu
         180             185             190

Gln Gln Ile Leu Leu Arg Arg Ile Gln Gly Ile Leu His Ala Gln Asn
         195             200             205

Phe Leu Met Leu Asp Tyr Asn Val Asp Arg Asp Asn Leu Asp Ala Ala
     210             215             220

Thr Ala Val Thr Pro Gly Leu Ser Gly Pro Thr Val Ser Pro Leu Ala
225             230             235             240

Arg Asp Asn Trp Val Ala Val Arg Ala Met Val Pro Arg Arg Ser Ala
             245             250             255

Asn Ala Ile Met Asp Lys Leu Ala Gly Leu Gly Ala Glu Ala Ile Leu
             260             265             270

Ala Ser Glu Ile Arg Ile Ala Arg Ile
         275             280
```

ATP PHOSPHORIBOSYLTRANSFERASE VARIANT AND METHOD FOR PRODUCING L-HISTIDINE USING THE SAME

SEQUENCE LISTING SUBMISSION VIA EFS-WEB

A computer readable text file, entitled "SequenceListing.txt," created on or about Sep. 10, 2020 with a file size of about 9 kb contains the sequence listing for this application and is hereby incorporated by reference in its entirety.

TECHNICAL FIELD

The present disclosure relates to an ATP phosphoribosyltransferase variant and a method for producing histidine using the same.

BACKGROUND ART

L-Histidine is one of the 20 standard amino acids, the majority of which, from a nutritional point of view, are not required for adults, but it is classified as an essential amino acid for growing children. Additionally, L-histidine is involved in important physiological processes such as anti-oxidation, immune regulation, etc., and thus is used in the medical industry (i.e., an agent for treating gastric ulcer, a raw material for a cardiovascular agent, amino acid sap, etc.)

Histidine is mainly found in hemoglobin, and is primarily produced by a protein hydrolysis extraction method using blood meal as a raw material. However, it has disadvantages such as low efficiency, environmental pollution, etc. On the other hand, L-histidine can be produced through microbial fermentation, but large-scale industrialization has not yet been accomplished. This is because the biosynthesis of L-histidine competes with the nucleotide synthesis precursor, i.e., PRPP, and has a complicated biosynthetic process and regulatory mechanism requiring high energy.

The L-histidine productivity of a microorganism used in a fermentation method has been improved by a mutagenic and mutant selection method and a method of regulating the metabolism of a strain through genetic modification. Recently, the production of histidine using microorganisms has been known to be accomplished by biosynthesis from PRPP via several steps. However, an ATP phosphoribosyltransferase, which is the first enzyme involved in the biosynthesis of histidine, has feedback inhibition by the final product, i.e., histidine, or a derivative thereof, and this is a problem in the mass production of L-histidine industrially (International Patent Publication No. WO2014-029376).

DISCLOSURE

Technical Problem

The present inventors have made intensive efforts to improve an ATP phosphoribosyltransferase inhibited by L-histidine, and as a result, they have found that a microorganism into which the newly developed ATP phosphoribosyltransferase variant is introduced can to produce L-histidine with a high yield, thereby completing the present disclosure.

Technical Solution

An objective of the present disclosure is to provide an ATP phosphoribosyltransferase variant having substitution of an asparagine at position 215 with arginine, substitution of glycine at position 233 with a histidine, and substitution of a threonine at position 235 with glutamine in amino acid sequence of SEQ ID NO: 13.

Another objective of the present disclosure is to provide a polynucleotide encoding the ATP phosphoribosyltransferase variant.

Still another objective of the present disclosure is to provide a vector comprising the polynucleotide encoding the ATP phosphoribosyltransferase variant.

Still another objective of the present disclosure is to provide a microorganism transformed to comprise the ATP phosphoribosyltransferase variant and the protein.

Still another objective of the present disclosure is to provide a method for producing histidine, comprising: culturing a microorganism in a medium; and recovering histidine from the cultured microorganism or culture medium.

Advantageous Effects

The present disclosure provides a method for efficiently producing histidine using an ATP phosphoribosyltransferase (HisG) protein.

BEST MODE

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the objectives above, an aspect of the present disclosure provides an ATP phosphoribosyltransferase variant having substitution of an asparagine at position 215 with arginine, substitution of glycine at position 233 with a histidine, and substitution of a threonine at position 235 with glutamine in amino acid sequence of SEQ ID NO: 13.

As used herein, the term "ATP phosphoribosyltransferase (HisG)" refers to a glycosyltransferase-family enzyme that catalyzes a chemical reaction, and particularly belongs to the pentosyltransferase enzyme family. The generic name for this enzyme is 1-(5-phospho-D-ribosyl)-ATP:diphosphate phospho-alpha-D-ribosyl transferase. The enzyme catalyzes the following reaction: 1-(5-phospho-D-ribosyl)-ATP+diphosphate ATP+5-phospho-alpha-D-ribose 1-diphosphate. The enzyme catalyzes the first step in the biosynthesis of histidine.

In the present disclosure, ATP phosphoribosyltransferase may be used interchangeably with "HisG" or "HisG protein". A sequence of the phosphoribosyltransferase may be obtained from a known database, i.e., GenBank of NCBI. For example, the ATP phosphoribosyltransferase may be ATP phosphoribosyltransferase derived from *Corynebacterium* sp., but is not limited thereto. For example, the ATP phosphoribosyltransferase may have an amino acid sequence of SEQ ID NO: 13, but is not limited thereto. For example, the ATP phosphoribosyltransferase may have an amino acid sequence of SEQ ID NO: 13 or an amino acid sequence having homology or identity to the sequence of SEQ ID NO: 13 of 80% or higher, but is not limited thereto. Specifically, the ATP phosphoribosyltransferase may include a polypeptide having a homology or identity to SEQ ID NOS: 13 and 1 of at least 80%, at least 85%, at least 90%, at least 95%, at least 96%, at least 97%, at least 98%, or at least 99%. Additionally, it is obvious that an auxiliary protein having an amino acid sequence with deletion, modification, substitution, or addition in part of the sequence can also be used as the ATP phosphoribosyltransferase of the present disclosure, as long as the amino acid sequence has a homology or identity described above and has an effect corresponding to that of the protein.

Specifically, the ATP phosphoribosyltransferase variant of the present disclosure may be one in which, in a *Corynebacterium*-derived ATP phosphoribosyltransferase having an amino acid sequence of SEQ ID NO: 13, a glycine amino acid residue at position 233, a threonine amino acid residue at position 235, or an asparagine amino acid residue at position 215 from the N-terminus is substituted with other amino acids. For example, the glycine amino acid residue at position 233 may be substituted with histidine; the threonine amino acid residue at position 235 may be substituted with glutamine; or the asparagine amino acid residue at position 215 may be substituted with arginine.

Specifically, the ATP phosphoribosyltransferase variant may consist of an amino acid sequence of SEQ ID NO: 1. In the present disclosure, the ATP phosphoribosyltransferase variant may include an amino acid sequence of SEQ ID NO: 1 or an amino acid sequence having a homology or identity to the amino acid sequence of SEQ ID NO: 1 of 80% or higher, but is not limited thereto. Specifically, the ATP phosphoribosyltransferase variant of the present disclosure may include a polypeptide of SEQ ID NO: 1 and a polypeptide having a homology or identity to the amino acid sequence of SEQ ID NO: 1 of at least 80%, at least 85%, at least 90%, at least 95%, at least 96%, at least 97%, at least 98%, or at least 99%. Additionally, it is obvious that an auxiliary protein having an amino acid sequence with deletion, modification, substitution, or addition in part of the sequence can also be included in the scope of the present disclosure, as long as the amino acid sequence has a homology or identity described above and has an effect corresponding to that of the protein.

Additionally, based on codon degeneracy, it is obvious that proteins which consist of the amino acid sequence of SEQ ID NO: 1, or polynucleotides which can be translated into proteins having a homology or identity to the above proteins, can also be included in the scope of the present disclosure. Additionally, any sequence which encodes a protein having the activity of a protein consisting of the amino acid sequence of SEQ ID NO: 1 that can be determined by hybridizing under stringent conditions with probe(s) that can be prepared from known gene sequences, for example, complementary sequence(s) to all or part of the above nucleotide sequence, can also be included without limitation in the scope of the present disclosure. The term "stringent conditions" refers to conditions under which specific hybridization between polynucleotides is made possible. Such conditions are specifically described in references (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). For example, the conditions may include performing hybridization between genes having a high homology, a homology or identity of 80% or higher, specifically 85% or higher, more specifically 90% or higher, even more specifically 95% or higher, even more specifically 97% or higher, and most specifically 99% or higher, while not performing hybridization between genes having a homology or identity of lower than the above homologies or identities; or to perform hybridization once, specifically two or three times, under conventional washing conditions for southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

That is, although described as "a protein or polypeptide having an amino acid sequence of a particular SEQ ID NO" in the present disclosure, the protein or polypeptide may have an activity that is identical or corresponding to that of a polypeptide consisting of an amino acid sequence of the corresponding SEQ ID NO. Is such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified polypeptide, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

The term "conservative substitution" refers to substitution of one amino acid with another amino acid having similar structural and/or chemical properties. Such an amino acid substitution may be generally made on the basis of similarity in polarity, charge, solubility, hydrophobicity, hydrophilicity, and/or the amphipathic nature of the residues involved. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

Therefore, in the present disclosure, the "variant" may include conservative substitution and/or modification of one or more amino acids in addition to "a protein or polypeptide having an amino acid sequence of a particular SEQ ID NO". For example, some variants may include variants in which one or more portions have been removed, such as a N-terminal leader sequence or a transmembrane domain. Other variants may include variants in which a portion has been removed from the N- and/or C-terminus. In addition, the variants may include other modifications, which include deletion or addition of amino acids having minimal impact on the properties and secondary structure of a polypeptide. For example, the polypeptide can be conjugated to a signal (or leader) sequence of a protein N-terminus that is involved in the transfer of proteins co-translationally or post-translationally. Additionally, the polypeptide may also be conjugated to another sequence or a linker to identify, purify, or synthesize the polypeptide. As used herein, the term "variant" may refer to a variant, modification, modified protein, modified polypeptide, mutant, mutein, divergent, etc., and is not limited as long as the term refers to modification.

Hybridization requires that two nucleic acids have a complementary sequence, although mismatches between bases may be possible depending on the stringency of the hybridization. The term "complementary" is used to describe the relationship between mutually hybridizable nucleotide bases. For example, with respect to DNA, adenosine is complementary to thymine, and cytosine is complementary to guanine. Accordingly, the present disclosure may also include isolated nucleic acid fragments complementary to the entire sequence as well as substantially similar nucleic acid sequences.

Specifically, polynucleotides having a homology or identity can be detected at a $T_m$ value of 55° C. using hybridization conditions that include a hybridization step and using the conditions described above. Additionally, the $T_m$ value may be 60° C., 63° C., or 65° C., but is not limited thereto and may be appropriately adjusted by an ordinary person skilled in the art according to the intended purpose.

The stringency suitable for the hybridization of polynucleotides depends on the length and complementarity of the polynucleotides, and the related variables are well known in the art (see Sambrook et al., supra, 9.50-9.51, 11.7-11.8).

The homology or identity refers to a degree of matching with a given amino acid sequence or nucleotide sequence, and may be expressed as a percentage.

The terms "homology" and "identity" may often be used interchangeably with each other.

The sequence homology or identity of conserved polynucleotide or polypeptide sequences may be determined by standard alignment algorithms and can be used with a default gap penalty established by the program being used. Substantially homologous or identical sequences are generally expected to hybridize under moderate or high stringency, along the entire length or at least about 50%, about 60%, about 70%, about 80%, or about 90% of the entire length of the sequences. Polynucleotides that contain degenerate codons instead of codons in the hybridizing polypeptides are also considered.

Whether any two polynucleotide or polypeptide sequences have a homology, similarity, or identity may be determined using a known computer algorithm such as the "FASTA" program (Pearson et al., (1988) [Proc. Natl. Acad. Sci. USA 85]: 2444: using default parameters in 2444). Alternately, it may be determined using the Needleman-Wunsch algorithm (Needleman and Wunsch, 1970, J. Mol. Biol. 48: 443-453), which is performed in the Needleman program of the EMBOSS package ((EMBOSS: The European Molecular Biology Open Software Suite, Rice et al., 2000, Trends Genet. 16: 276-277) (version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, the homology, similarity, or identity may be determined using BLAST or ClustalW of the National Center for Biotechnology Information (NCBI).

The homology, similarity, or identity of polynucleotide or polypeptide sequences may be determined by comparing sequence information using, for example, the GAP computer program (e.g., Needleman et al., (1970), J Mol Biol. 48: 443) as published (e.g., Smith and Waterman, Adv. Appl. Math (1981) 2:482). In summary, the GAP program defines the homology, similarity, or identity as the value obtained by dividing the number of similarly aligned symbols (i.e., nucleotides or amino acids) into the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), Nucl. Acids Res. 14:6745, as disclosed in Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences.

Another aspect of the present disclosure provides a polynucleotide encoding the ATP phosphoribosyltransferase variant, or a vector comprising the polynucleotide.

As used herein, the term "polynucleotide" refers to a nucleotide polymer composed of nucleotide monomers covalently bonded in a chain, and examples thereof are DNA or RNA strands having a predetermined or longer length. Specifically, the polynucleotide refers to a polynucleotide fragment encoding the modified polypeptide.

In the present disclosure, the gene encoding the amino acid sequence of the ATP phosphoribosyltransferase is a hisG gene, which may be specifically derived from *Corynebacterium glutamicum*. Based on genetic code degeneracy, nucleotide sequences encoding the same amino acid sequence and variants thereof belong to the scope of the present disclosure, and specifically, they may be represented by SEQ ID NO: 2, but are not limited thereto.

Additionally, with respect to the modified polypeptide, nucleotide sequences encoding the same amino acid and variants thereof also belong to the scope of the present disclosure based on genetic code degeneracy.

Still another aspect of the present disclosure provides a host cell comprising the polynucleotide encoding the ATP phosphoribosyltransferase variant, and a microorganism transformed with a vector comprising the polynucleotide encoding the ATP phosphoribosyltransferase variant. Specifically, the introduction may be carried out by transformation, but is not limited thereto.

Specifically, in the microorganisms comprising the ATP phosphoribosyltransferase variant of the present disclosure, the histidine-producing ability is improved without inhibiting the growth of a host cell compared to a microorganism comprising a wild-type ATP phosphoribosyltransferase. Therefore, histidine can be obtained in high yield from these microorganisms.

As used herein, the term "vector" refers to a DNA construct including the nucleotide sequence of the polynucleotide encoding a target protein, in which the target protein is operably linked to a suitable control sequence so that it can be expressed in an appropriate host. The control sequence includes a promoter capable of initiating transcription, any operator sequence for the control of the transcription, a sequence encoding an appropriate mRNA ribosome-binding domain, and a sequence controlling the termination of transcription and translation. The vector, after being transformed with a suitable host cell, may be replicated or function irrespective of the host genome, or may be integrated into the host genome itself.

The vector used in the present disclosure is not particularly limited, as long as it is able to replicate in the host cell, and any vector known in the art may be used. Examples of conventional vectors may include a natural or recombinant plasmid, cosmid, virus and bacteriophage. For instance, pWE15, M13, MBL3, MBL4, IXII, ASHII, APII, t10, t11, Charon4A, and Charon21A may be used as a phage vector or cosmid vector; and pBR type, pUC type, pBluescriptII type, pGEM type, pTZ type, pCL type and pET type may be used as a plasmid vector. A vector usable in the present disclosure is not particularly limited, and any known expression vector may be used. Specifically, pDZ, pACYC177, pACYC184, pCL, pECCG117, pUC19, pBR322, pMW118, or pCC1BAC vector may be used.

In an embodiment, a polynucleotide encoding a target protein in the chromosome may be replaced with a modified polynucleotide through a vector for chromosomal insertion. The insertion of the polynucleotide into the chromosome may be performed by any method known in the art (e.g., homologous recombination), but the method is not limited thereto.

As used herein, the term "transformation" refers to a process of introducing into a host cell a vector including a polynucleotide encoding a target protein, thereby enabling the expression of the protein encoded by the polynucleotide in the host cell. For the transformed polynucleotide, it does not matter whether the transformed polynucleotide is inserted into the chromosome of a host cell and located therein or located outside the chromosome, as long as it can be expressed in the host cell, and both cases are included. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as is and operably linked to a sequence essential for its expression in the host cell, but the polynucleotide is not limited thereto.

Additionally, as used herein, the term "operably linked" refers to a functional linkage between a promoter sequence, which initiates and mediates the transcription of the polynucleotide encoding the target protein of the present disclosure, and the above gene sequence.

As used herein, the term "histidine-producing microorganism" or "microorganism having histidine productivity" refers to a microorganism naturally having a histidine-producing ability or a microorganism in which a histidine-producing ability is provided to its parent strain having no histidine-producing ability.

The histidine-producing microorganism may be a cell or microorganism which includes a polynucleotide encoding a modified polypeptide or which is capable of expressing a modified polypeptide by transforming into a vector including a polynucleotide encoding a modified polypeptide. For the objectives of the present disclosure, the host cell or microorganism may be any microorganism capable of producing L-histidine, which includes the ATP phosphoribosyltransferase variant. For example, the microorganism may be a microbial strain such as *Escherichia* sp., *Serratia* sp., *Erwinia* sp., *Enterobacteria* sp., *Salmonella* sp., *Streptomyces* sp., *Pseudomonas* sp., *Brevibacterium* sp., or *Corynebacterium* sp., specifically may be a microorganism of the genus *Corynebacterium*, and more specifically may be *Corynebacterium glutamicum*, but the microorganism is not limited thereto.

As used herein, the term "histidine-producing microorganism of the genus *Corynebacterium* producing histidine" refers to a microorganism of the genus *Corynebacterium*, which has a histidine-producing ability naturally or by modification. It is already known that histidine is included in a culture of a microorganism of the genus *Corynebacterium*. However, its histidine-producing ability is remarkably low, and genes or mechanisms involved in the production have not yet been revealed. Therefore, the "microorganism of the genus *Corynebacterium* having histidine-producing ability" in the present disclosure refers to a native microorganism itself or a microorganism of the genus *Corynebacterium* in which a foreign gene involved in the histidine production mechanism is inserted or activity of an endogenous gene is reinforced or inactivated so as to have an improved histidine-producing ability.

As used herein, the "microorganism of the genus *Corynebacterium*" may be specifically *Corynebacterium glutamicum, Corynebacterium ammoniagenes, Brevibacterium lactofermentum, Brevibacterium flavum, Corynebacterium thermoaminogenes, Corynebacterium efficiens*, etc., but is not limited thereto. More specifically, the microorganism of the genus *Corynebacterium* may be *Corynebacterium glutamicum*, the cell growth and survival of which are hardly affected even when exposed to a high concentration of histidine.

Still another aspect of the present disclosure provides a method for producing histidine, comprising: culturing the microorganism described in the present disclosure; and recovering histidine from the cultured microorganism or cultured medium.

In the method, the step of culturing the microorganism may be performed by batch culture, continuous culture, and fed-batch culture known in the art, but is not particularly limited thereto. Herein, the culture conditions are not particularly limited, but an optimal pH (e.g., pH 5 to 9, specifically pH 6 to 8, and most specifically pH 6.8) may be maintained by using a basic chemical (e.g., sodium hydroxide, potassium hydroxide, or ammonia) or an acidic chemical (e.g., phosphoric acid or sulfuric acid). In addition, an aerobic condition may be maintained by adding oxygen or an oxygen-containing gas mixture to a cell culture. The culture temperature may be maintained at 20° C. to 45° C., and specifically at 25° C. to 40° C., and the cultivation may be performed for about 10 hours to 160 hours, but the conditions are not limited thereto. The histidine produced by the culture may be secreted into a medium or may remain in cells.

Additionally, a medium to be used for culture may include sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid) individually or in combination as a carbon source; a nitrogen-containing organic compound (e.g., peptone, yeast extract, meat juice, malt extract, corn solution, soybean meal powder, and urea) or an inorganic compound (e.g., ammonium sulfate, ammonium chloride, ammonium phosphate, ammonium carbonate, and ammonium nitrate) individually or in combination as a nitrogen source; and potassium dihydrogen phosphate, dipotassium phosphate, or a sodium-containing salt corresponding thereto individually or in combination as a phosphorous source; but these are not limited thereto. In addition, the medium may contain essential growth-promoting materials such as other metal salts (e.g., magnesium sulfate or iron sulfate), amino acids, and vitamins.

The method for recovering the histidine produced in the culture step of the present disclosure may be carried out to collect a target amino acid from the cultured medium by using a suitable method known in the art according to the culture method. For example, centrifugation, filtration, anion-exchange chromatography, crystallization, and HPLC may be used, and the target histidine may be recovered from the medium or microorganism by using a suitable method known in the art.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Design of ATP Phosphoribosyltransferase (HisG) Variant

In an ATP phosphoribosyltransferase (HisG) of a microorganism of the genus *Corynebacterium*, when the concentrations of histidine, purine-type nucleotide, etc. are increased, ATP, which is a substrate, competitively or uncompetitively binds to a regulatory domain of the ATP phosphoribosyltransferase, and thereby its activity is weakened. Based on this, a variant which structurally enhances its activity while preventing the binding of histidine to the ATP phosphoribosyltransferase was designed.

Specifically, an ATP phosphoribosyltransferase variant (N215R/G233H/T235Q, SEQ ID NO: 1) was designed in which, from the N-terminus of a *Corynebacterium glutamicum* ATP phosphoribosyltransferase, a glycine amino acid residue at position 233 is substituted with histidine, a threonine amino acid residue at position 235 is substituted with glutamine, and an asparagine amino acid residue at position 215 is substituted with arginine. The nucleotide sequence encoding the ATP phosphoribosyltransferase variant of SEQ ID NO: 1 is SEQ ID NO: 2.

Example 2: Cloning of hisG Gene, and Construct of Vector for Chromosomal Insertion for Preparing Markerless Strains

Example 2-1: Cloning of HisG Gene Into Which N215R Variation and G233H and T235Q Variation are Introduced, and Construct of Vector for Chromosomal Insertion Chromosomal genes of wild-type *Corynebacterium glutamicum* ATCC13032 were isolated, and then hisG gene fragments were obtained through polymerase chain reaction using primer pairs of SEQ ID NOS: 3 and 4 (Table 1). Herein, after denaturation at 95° C. for 5 minutes, PCR was carried out for a total of 25 cycles under the following conditions: denaturation at 95° C. for 30 seconds, annealing at 52° C. for 30 seconds, and polymerization at 72° C. for 90 seconds. Thereafter, the polymerization reaction was carried out at 72° C. for 7 minutes. As a result, polynucleotides (about 850 bp) were obtained. The thus-obtained hisG gene fragments were ligated to a TOPO vector, and the constructed vector was named as pTOPO-hisG.

TABLE 1

| SEQ ID NO: | Primer | Sequence (5'-3') |
|---|---|---|
| 3 | XbaI-Cgl-hisG-F | GGGTCTAGACCCAAACAAAGGCTCGC |
| 4 | XbaI-Cgl-hisG-R | GGGTCTAGAGCAAGGTTGGCAACAACC |

PCR was carried out with the primers described in Tables 1 and 2 using the prepared pTOPO-hisG vector as a template, as follows. Centering on a region to be modified for the introduction of a variation in hisG genes, primary PCR was carried out for the 5' and 3' termini, respectively, and then secondary PCR was carried out to combine the two PCR fragments.

Specifically, the 5' terminus of the template was amplified by PCR using primers of XbaI-Cgl-hisG-F (SEQ ID NO: 3) and Cgl-hisG-G233H/T235Q-R (SEQ ID NO: 8). The 3' terminus of the template was amplified by PCR using primers of Cgl-hisG-G233H/T235Q-F (SEQ ID NO: 7) and XbaI-Cgl-hisG-R (SEQ ID NO: 4). Secondary PCR was carried out with the primers of XbaI-Cgl-hisG-F (SEQ ID NO: 3) and XbaI-Cgl-hisG-R (SEQ ID NO: 4) using the two PCR fragments obtained by PCR as a template for the secondary PCR. The fragments of the hisG_G233H/T235Q genes obtained by the secondary PCR were cleaved by a restriction enzyme XbaI (New England Biolabs, Beverly, Mass.). A recombinant vector was constructed by ligating the cleaved gene fragments to a linear vector, in which the pDC vector for chromosomal insertion had been digested with a restriction enzyme XbaI, by using T4 ligase (New England Biolabs, Beverly, Mass.). The constructed vector was named as pDC-hisG_G233H/T235Q.

In order to further introduce the N215R variation, secondary PCR was carried out once again. Specifically, using pDC-hisG_G233H/T235Q as a template, the 5' terminus was amplified by PCR with primers of Cgl13032 hisG N215R-F (SEQ ID NO: 5) and Cgl-hisG-G233H/T235Q-R (SEQ ID NO: 8); and the 3' terminus was amplified by PCR with primers of Cgl-hisG-G233H/T235Q-F (SEQ ID NO: 7) and Cgl13032 hisG N215R-R (SEQ ID NO: 6). Secondary PCR was carried out with the primers of XbaI-Cgl-hisG-F (SEQ ID NO: 3) and XbaI-Cgl-hisG-R (SEQ ID NO: 4) using the two amplified PCR fragments as a template for the secondary PCR. The gene fragments obtained by the secondary PCR were cleaved by a restriction enzyme XbaI, and the cleaved gene fragments were ligated to a linear vector in which the pDC vector for chromosomal insertion had been digested with a restriction enzyme XbaI. Thereafter, the results were then inserted into the pDC vector. The constructed vector was named as pDC-hisG_N215R/G233H/T235Q. Whether the hisG variation was introduced into the thus-constructed vector was confirmed by sequence analysis.

Example 2-2: Cloning of Gene into which Known HisG is Introduced, and Construct of Vector for Chromosomal Insertion In order to compare the histidine-producing ability of a microorganism, into which a known HisG-modified gene (N215K/L231F/T235A) is introduced, with that of a microorganism, into which the variation of the present disclosure is introduced, a vector of a known modified gene was constructed (Biochimie. 2012 March; 94(3):829-38).

In order to construct a vector into which a HisG-modified gene (N215K/L231F/T235A) is introduced, in the same manner as in Example 2-1, PCR amplification was carried out with each of primers of SEQ ID NOS: 9 and 12 and SEQ ID NOS: 10 and 11 using the pTOPO template vector as a template (Table 2). Using the two amplified PCR fragments as a template for secondary PCR, the secondary PCR was carried out with the primers of XbaI-Cgl-hisG-F (SEQ ID NO: 3) and XbaI-Cgl-hisG-R (SEQ ID NO: 4). The gene fragments obtained from the secondary PCR were cleaved by a restriction enzyme Xba1, and the cleaved gene fragments were ligated to a linear vector in which the pDC vector for chromosomal insertion had been digested with a restriction enzyme XbaI. Thereafter, the results were then inserted into the PDC vector. The thus-constructed vector was named as pDC-hisG_N215K/L231F/T235A.

TABLE 2

| SEQ ID NO: | Primer | Sequence (5'-3') |
|---|---|---|
| 5 | Cgl13032 hisG N215R-F | CCTCATGCTGGATTACCGCGTCG |
| 6 | Cgl13032 hisG N215R-R | CGACGCGGTAATCCAGCATGAGG |
| 7 | Cgl-hisG-G233H/T235Q-F | CAGGCTTATCCCACCCACAGGTATCCCCAC |
| 8 | Cgl-hisG-G233H/T235Q-R | GTGGGGATACCTGTGGGTGGGATAAGCCTG |
| 9 | Cgl-hisG-N215K-F | GCTGGATTACAAGGTCGACCGCGAC |
| 10 | Cgl-hisG-N215K-R | GTCGCGGTCGACCTTGTAATCCAGC |
| 11 | Cgl-hisG-L231F/T235A-F | ACCCCAGGCTTCTCCGGCCCAGCAGTATCCCCACT |
| 12 | Cgl-hisG-L231F/T235A-R | AGTGGGGATACTGCTGGGCCGGAGAAGCCTGGGGT |

Example 3: Selection of Strain Inserted with HisG-Modified Gene

Example 3-1: Selection of Wild-Type Strain Inserted with HisG-Modified Gene The hisG_N215R/G233H/T235Q vector containing the HisG-modified gene, which was constructed in Example 2, was transformed with wild-type *Corynebacterium glutamicum* ATCC 13032 by electroporation. Thereafter, strains exhibiting resistance were selected from a selective medium containing kanamycin (25 mg/L). A secondary recombinant process (cross-over) was carried out in order to select the strains in which the modified gene is inserted on the chromosome. PCR was carried out using the primers of Xba1-Cgl-hisG-F (SEQ ID NO: 3) and Xba1-Cgl-hisG-R (SEQ ID NO: 4). The strain, into which the hisG-modified gene is inserted by the DNA fragment hisG_N215R/G233H/T235Q inserted on the genome, was confirmed by sequence analysis of the PCR products, and it was named as ATCC13032-161.

Example 3-2: Selection of Strain Having L-Histidine-Producing Ability, into which Vector Including HisG-Modified Gene is Inserted

*Corynebacterium glutamicum* ATCC 13032 cannot produce histidine. Therefore, in order to measure the activity of the enzyme and confirm the L-histidine-producing ability, HCJ-86 (KCCM11795P), which is a strain having L-histidine-producing ability, was used as a host cell.

The HCJ-86 was obtained as follows. After culture and inactivation for 16 hours in a wild-type *Corynebacterium glutamicum* activation medium, the activated strain was inoculated into a seed medium sterilized at 121° C. for 15 minutes, and then cultured for 14 hours. Thereafter, the culture medium (5 mL) was recovered. The recovered culture medium was washed with a citric acid buffer (100 mM), N-methyl-N'-nitro-N-nitrosoguanidine (NTG) was added to a final concentration of 200 mg/L, and then the resultants were treated for 20 minutes. Thereafter, the resultants were washed with a phosphate buffer (100 mM). The mortality rate was calculated by smearing the strain treated with NTG on a minimal medium, and it was found that the mortality rate was 85%.

One variant, which has resistance to 1,2,4-triazole-3-alanine, e.g., a derivative of L-histidine, and which has an L-histidine-producing ability, was selected. The variant was named as HCJ-86. The HCJ-86 variant was deposited to the Korea Culture Center of Microorganisms, which is an international depositary authority under the Budapest Treaty, on Dec. 22, 2015, and assigned Accession No. KCCM11795P. Sequence analysis of the hisG gene of HCJ-86 revealed that the sequence was identical to that of wild-type *Corynebacterium glutamicum* ATCC 13032. Therefore, it was confirmed that there was no variation in the hisG gene.

The pDC-hisG_G233H/T235Q, pDC-hisG_N215R/G233H/T235Q, and pDC-hisG_N215K/L231F/T235A vectors containing the HisG-modified gene, which had been constructed in Example 2, were transformed with *Corynebacterium glutamicum* HCJ-86 by electroporation. Thereafter, strains exhibiting resistance were selected from a selective medium containing kanamycin (25 mg/L). A secondary recombinant process (cross-over) was carried out in order to select the strains in which the modified gene is inserted on the chromosome. PCR was carried out using the primers of Xba1-Cgl-hisG-F (SEQ ID NO: 3) and Xba1-Cgl-hisG-R (SEQ ID NO: 4). The strains, in which the hisG gene is modified by the DNA fragments hisG_G233H/T235Q, hisG_N215R/G233H/T235Q, and hisG_N215K/L231F/T235A inserted on the genome, were obtained and it was confirmed by sequence analysis of the PCR products. These were named as HCJ-96, HCJ-161, and HCJ-162, respectively.

Among these, the HCJ-161 was deposited to the Korea Culture Center of Microorganisms (KCCM), which is an international depositary authority under the Budapest Treaty, on Feb. 27, 2017, and assigned Accession No. KCCM11982P.

Additionally, the sequences of the strains that had undergone the secondary recombinant process (cross-over) were analyzed to select a strain having only a hisG_N215R DNA fragment, and this was named as HCJ-163.

In order to construct a strain having the hisG_N215R/L231F/T235A modification, the HCJ-161 strain was transformed with the pDC-hisG_N215K/L231F/T235A vector by electroporation. Thereafter, strains showing resistance were primarily selected from a selective medium containing kanamycin (25 mg/L). The sequences of the strains that had undergone the secondary recombinant process (cross-over) were analyzed, and a strain containing the hisG_N215R/L231F/T235A modification was secondarily selected from the strains in which the recombination had occurred in the hisG gene. The selected strain was named as HCJ-164.

In order to prepare a strain having the hisG_N215K/G233H/T235Q modification, the HCJ-162 strain was transformed with the pDC-hisG_G233H/T235Q vector by electroporation. Thereafter, strains showing resistance were primarily selected from a selective medium containing kanamycin (25 mg/L). The sequences of the strains that had undergone the secondary recombinant process (cross-over) were analyzed, and a strain containing the hisG_N215K/G233H/T235Q modification was secondarily selected from the strains in which the recombination had occurred in the hisG gene. The selected strain was named as HCJ-165. Each strain and the ATP phosphoribosyltransferase (HisG) modification traits are shown in Table 3 below.

TABLE 3

| Strain | HisG Modification Trait |
| --- | --- |
| HCJ-96 | HisG (G233H/T235Q) |
| HCJ-161 | HisG (N215R/G233H/T235Q) |
| HCJ-162 | HisG (N215K/L231F/T235A) |
| HCJ-163 | HisG (N215R) |
| HCJ-164 | HisG (N215R/L231F/T235A) |
| HCJ-165 | HisG (N215K/G233H/T235Q) |

Example 4: Measurement of Activities of ATP Phosphoribosyltransferases

Example 4-1: Obtaining of ATP Phosphoribosyltransferase

*Corynebacterium glutamicum* ATCC 13032 and the strains HCJ-96, HCJ-161, HCJ-162, HCJ-163, HCJ-164, and HCJ-165 selected in Example 3 were each inoculated into a corner-baffle flask (250 mL) containing a seed medium (25 mL), and were cultured at 30° C. for 20 hours with shaking at 200 rpm to obtain a seed culture solution. Thereafter, the seed culture solution (1 mL) was inoculated into a corner-baffle flask (250 mL) containing a production medium (24 mL), and was cultured at 30° C. for 45 hours at 200 rpm. After the culture, the obtained cells were sonicated and centrifuged, and the supernatant obtained therefrom was used for evaluation of the activity of ATP phosphoribosyltransferase. Meanwhile, the compositions of the media used in Example 4-1 are shown in Table 4 below.

TABLE 4

| Type | Composition and pH of medium |
| --- | --- |
| Seed medium | glucose (5%), bactopeptone (1%), sodium chloride (0.25%), yeast extract (1%), urea (0.4%); pH 7.2 |
| Production medium | glucose (5%), ammonium sulfate (2%), monobasic potassium phosphate (0.1%), magnesium sulfate heptahydrate (0.05%), corn steep liquor (CSL, 2.0%), biotin (200 μg/L), calcium carbonate (30 g); pH 7.2 |

Example 4-2: Measurement of Activities of ATP Phosphoribosyltransferases

The activities of the ATP phosphoribosyltransferase variants obtained in Example 4-1 and that of a wild-type ATP phosphoribosyltransferase variant were measured. The evaluation of the activities of these enzymes was performed with reference to the conditions described in an existing literature report (Biochimie. 2012 March; 94(3):829-38.).

For the evaluation of the activities of the enzymes, the supernatant was quantified to give the same concentration. These enzymes were used as sample enzymes, and the reaction conditions were as follows: the reaction compositions were mixed to the quantified protein (0.05 mg) to give a total amount of 500 μL, and then measured at 30° C. at a UV wavelength of 290 nm for 90 seconds. With regard to the wild-type ATP phosphoribosyltransferase having low activity, the supernatant protein (0.3 mg) was used and measured at a UV wavelength of 290 nm for 30 minutes for the activity evaluation. The composition of the reaction solution for measuring the activities of the enzymes is as follows:

TABLE 5

| Reaction composition |
| --- |
| 100 mM Tris, pH 8.5 |
| 150 mM KCl |
| 10 mM MgCl |
| 5 mM ATP |
| 0.5 mM PRPP |
| 1 U yeast pyrophosphatase |
| ATP phosphoribosyltransferase + DDW |
| Total                                500 μL |

As a result of the measurement, it was confirmed that the ATP phosphoribosyltransferase variants had activities that are enhanced compared to that of the wild-type ATP phosphoribosyltransferase. In particular, the ATP phosphoribosyltransferase variant having the N215R/G233H/T235Q variation exhibited an activity about 160-fold higher than that of the wild-type enzyme (Table 6).

TABLE 6

| Activity of ATP phosphoribosyltransferase (HisG) | |
| --- | --- |
| Type of Enzyme | Activity (U/mg) |
| HisG | 0.013 |
| HisG (G233H/T235Q) | 1.381 |
| HisG (N215R/G233H/T235Q) | 2.082 |
| HisG (N215K/L231F/T235A) | 0.387 |
| HisG (N215R) | 0.021 |
| HisG (N215R/L231F/T235A) | 0.408 |
| HisG (N215K/G233H/T235Q) | 1.3 |

Example 4-3: Measurement of Degree of Inhibition by Histidine on Activities of ATP Phosphoribosyltransferase Variants The degree of inhibition by L-histidine on the activities of ATP phosphoribosyltransferase and the ATP phosphoribosyltransferase variants obtained in Example 4-1 was measured. Specifically, the activities of these enzymes were measured in the reaction composition solution of Example 4-2, which contained L-histidine (0 mM, 50 mM, or 100 mM), using the method described in Example 4-2. As a result of the measurement, it was confirmed that the activity of the wild-type enzyme was completely inhibited at L-histidine concentrations of 50 mM and 100 mM. However, the activities of the ATP phosphoribosyltransferase variants were less inhibited by L-histidine. In particular, the ATP phosphoribosyltransferase variant having the N215R/G233H/T235Q variation showed the highest activity even in the composition solution containing L-histidine (100 mM) (Table 7).

TABLE 7

Inhibition of ATP phosphoribosyltransferase (HisG) activity by L-histidine

| | Activity of Enzyme (U/mg) | | |
|---|---|---|---|
| | 0 mM | 50 mM | 100 mM |
| HisG | 0.013 | 0 | 0 |
| HisG (G233H/T235Q) | 1.381 | 0.64 | 0.542 |
| HisG (N215R/G233H/T235Q) | 2.082 | 1.435 | 1.335 |
| HisG (N215K/L231F/T235A) | 0.387 | 0.202 | 0.023 |
| HisG (N215R) | 0.021 | 0 | 0 |
| HisG (N215R/L231F/T235A) | 0.408 | 0.157 | 0 |
| HisG (N215K/G233H/T235Q) | 1.3 | 0.679 | 0.413 |

Example 5: Measurement of L-Histidine-Producing Ability of L-Histidine-Producing Strain into which ATP Phosphoribosyltransferase Variant is Introduced L-Histidine-producing abilities of the strains selected in Example 3 were measured to confirm the effects of the ATP phosphoribosyltransferase variants having increased activities on the production of L-histidine.

The *Corynebacterium glutamicum* ATCC 13032, which is a parent strain, and the variants ATCC13032-161, HCJ-96, HCJ-161, HCJ-162, HCJ-163, HCJ-164, and HCJ-165 were each inoculated into a corner-baffle flask (250 mL) containing a seed medium (25 mL), and were cultured at 30° C. for 20 hours with shaking at 200 rpm to obtain a seed culture solution. Thereafter, the seed culture solution (1 mL) was inoculated into a corner-baffle flask (250 mL) containing a production medium (24 mL), and was cultured at 30° C. for 45 hours at 200 rpm to produce L-histidine. After completion of the culture, the amount of L-histidine production was measured using high-performance liquid chromatography (HPLC). Detailed analytical methods and concentrations are shown in Table 8 below.

TABLE 8

| Analysis Item | Histidine |
|---|---|
| Concentration of STD | STD 1: 0.011 g/L |
| | STD 2: 0.033 g/L |
| | STD 3: 0.100 g/L |
| Mobile Phase | A: 25 mM-$KH_2PO_4$ + 12 mM-Octane sulfonic acid sodium salt pH 2.5 (by $H_3PO_4$) |
| | B: 25 mM-$KH_2PO_4$ + 12 mM-Octane sulfonic acid sodium salt: Acetonitrile = 50:50 pH 2.5 (by $H_3PO_4$) |
| | A:B = 80:20 |

TABLE 8-continued

| Analysis Item | | Histidine |
|---|---|---|
| Analysis Condition | System | HPLC |
| | Amount of Sample Injected | 5 μL |
| | Flow Rate | 1.0 mL/min |
| | Column | CAP CELL PAK C18 (ACR) 3 μm, 4.6 × 150 mm |
| | Column Temperature | 40° C. |
| | Detector | UV 210 nm |
| | Run Time | 12 min |

TABLE 9

| Strain | Concentration of L-histidine (g/L) |
|---|---|
| *Corynebacterium glutamicum* ATCC 13032 | 0 |
| ATCC 13032 -161 | 0.5 |
| HCJ-86 | 1.6 |
| HCJ-96 [hisG (G233H/T235Q)] | 1.9 |
| HCJ-161 [hisG (N215R/G233H/T235Q)] | 2.3 |
| HCJ-162 [hisG (N215K/L231F/T235A)] | 1.6 |
| HCJ-163 [hisG (N215R)] | 1.6 |
| HCJ-164 [hisG (N215R/L231F/T235A)] | 1.5 |
| HCJ-165 [hisG (N215K/G233H/T235Q)] | 2.1 |

As a result, it was confirmed that the wild-type *Corynebacterium glutamicum* ATCC 13032 did not in any way produce L-histidine, and that the ATCC 13032-161 transformed with the ATP phosphoribosyltransferase variant of the present disclosure produced L-histidine (0.5 g/L). Additionally, the HCJ-161 produced L-histidine (2.3 g/L), the amount of which was higher than that of the HCJ-86, a parent strain, by 43.75% (Table 9). It was confirmed that the HCJ-86, HCJ-96, HCJ-162, HCJ-163, and HCJ-164 strains all produced histidine at levels of 1.6 g/L to 1.9 g/L, and that the HCJ-161 strain having the ATP phosphoribosyltransferase variant (N215R/G233H/T235Q) showed the highest enzyme activity and L-histidine-producing ability. As a result, it was confirmed that L-histidine can be produced with high efficiency and high yield by using the ATP phosphoribosyltransferase variant (N215R/G233H/T235Q) of the present disclosure.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. An ATP phosphoribosyltransferase variant having a substitution of an asparagine at position corresponding to 215 with arginine, a substitution of glycine at position corresponding to 233 with a histidine, and a substitution of a threonine at position corresponding to 235 with glutamine in the amino acid sequence of SEQ ID NO: 13, wherein the variant comprises an amino acid sequence having at least 95% sequence identity to SEQ ID NO: 13, wherein the ATP phosphoribosyltransferase variant has ATP phosphoribosyltransferase activity.

2. The ATP phosphoribosyltransferase variant of claim 1, wherein the ATP phosphoribosyltransferase variant consists of the amino acid sequence of SEQ ID NO: 1.

3. A polynucleotide encoding an ATP phosphoribosyltransferase variant, wherein the ATP phosphoribosyltransferase variant has a substitution of an asparagine at position corresponding to 215 with arginine, a substitution of glycine at position corresponding to 233 with a histidine, and a substitution of a threonine at position corresponding to 235 with glutamine in the amino acid sequence of SEQ ID NO: 13, and the variant comprises an amino acid sequence having at least 95% sequence identity to SEQ ID NO: 13, wherein the ATP phosphoribosyltransferase variant has ATP phosphoribosyltransferase activity.

4. A vector comprising the polynucleotide of claim 3.

5. A microorganism of the genus *Corynebacterium*, wherein the microorganism comprises at least one selected from the group consisting of
   (a) an ATP phosphoribosyltransferase variant;
   (b) a polynucleotide encoding the ATP phosphoribosyltransferase variant; and
   (c) a vector comprising the polynucleotide encoding the ATP phosphoribosyltransferase variant,
   wherein the ATP phosphoribosyltransferase variant has a substitution of an asparagine at position corresponding to 215 with arginine, a substitution of glycine at position corresponding to 233 with a histidine, and a substitution of a threonine at position corresponding to 235 with glutamine in the amino acid sequence of SEQ ID NO: 13, and the variant comprises an amino acid sequence having at least 95% sequence identity to SEQ ID NO: 13, and the ATP phosphoribosyltransferase variant has ATP phosphoribosyltransferase activity.

6. The microorganism of claim 5, wherein the microorganism of the genus *Corynebacterium* is *Corynebacterium glutamicum*.

7. A method for producing histidine, comprising:
culturing the microorganism of claim 5 in a medium; and
recovering histidine from the cultured microorganism or culture medium.

8. The method of claim 7, wherein the microorganism of the genus *Corynebacterium* is *Corynebacterium glutamicum*.

9. The polynucleotide of claim 3, wherein the ATP phosphoribosyltransferase variant consists of the amino acid sequence of SEQ ID NO: 1.

10. A microorganism transformed with a polynucleotide encoding an ATP phosphoribosyltransferase variant consisting of the amino acid sequence of SEQ ID NO: 1.

11. The microorganism of claim 10, wherein the microorganism is *Corynebacterium glutamicum*.

12. A method of producing histidine comprising culturing the microorganism of claim 10.

13. The method of claim 12, wherein the microorganism is *Corynebacterium glutamicum*.

14. The microorganism of claim 10, wherein the microorganism is of the genus *Corynebacterium*.

15. The method of claim 12, wherein the microorganism is of the genus *Corynebacterium*.

\* \* \* \* \*